(12) United States Patent
Nazzaro et al.

(10) Patent No.: US 7,998,108 B2
(45) Date of Patent: Aug. 16, 2011

(54) INJECTOR APPARATUS AND METHOD OF USE

(75) Inventors: Martin Nazzaro, Quincy, MA (US); Hong Guo, Belmont, MA (US); Ron LeBlanc, Hopedale, MA (US); Josh York, Ipswich, MA (US)

(73) Assignee: pSivida US, Inc., Watertown, MA (US)

( * ) Notice: Subject to any disclaimer, the term of this patent is extended or adjusted under 35 U.S.C. 154(b) by 122 days.

(21) Appl. No.: 11/900,907

(22) Filed: Sep. 12, 2007

(65) Prior Publication Data
US 2008/0071246 A1 Mar. 20, 2008

Related U.S. Application Data

(60) Provisional application No. 60/844,261, filed on Sep. 12, 2006.

(51) Int. Cl.
*A61M 31/00* (2006.01)
(52) U.S. Cl. .......................................... 604/60; 604/506
(58) Field of Classification Search .................. 604/181, 604/187, 60, 506
See application file for complete search history.

(56) References Cited

U.S. PATENT DOCUMENTS

| | | | |
|---|---|---|---|
| 3,483,810 A | 12/1969 | Peters et al. | |
| 5,250,026 A | 10/1993 | Ehrlich et al. | |
| 7,468,065 B2 * | 12/2008 | Weber et al. | 606/107 |
| 2003/0004457 A1 | 1/2003 | Andersson | |
| 2003/0093084 A1 * | 5/2003 | Nissan et al. | 606/108 |

FOREIGN PATENT DOCUMENTS

| | | |
|---|---|---|
| EP | 0639387 A1 | 2/1995 |
| WO | WO-99/53991 | 10/1999 |
| WO | WO0-2004/026106 A2 | 4/2004 |

OTHER PUBLICATIONS

International Search Report for PCT/US2007/019860 dated Jan. 15, 2008.

* cited by examiner

*Primary Examiner* — Theodore J Stigell
*Assistant Examiner* — Imani Hayman
(74) *Attorney, Agent, or Firm* — Ropes & Gray LLP (57) ABSTRACT

Disclosed herein is an injector device including an inserter element, a head element, an implant and a set of detachable protector elements for secured device handling. The device comprises a stop that controls the penetration depth of the device during injection. The device may comprise a removable catch that prevents the implant from exiting the device due to the advancement of its inserter element. The device may comprise a disengageable block that prevents the implant from exiting the device from its head element. The device may be configured for intraocular drug delivery.

24 Claims, 7 Drawing Sheets

INJECTOR APPARATUS AND METHOD OF USE

CROSS-REFERENCE TO RELATED APPLICATIONS

This application claims the benefit of U.S. Provisional Application No. 60/844,261, filed Sep. 12, 2006, the specification of which is hereby incorporated by reference in its entirety.

BACKGROUND OF THE INVENTION

The human eye is a highly evolved and complex sensory organ. Damages to any of its essential structures can result in impairment of vision. Treatments of various eye conditions and diseases often consist of applying doses of appropriate medications in aqueous suspension solutions or ointments. While such treatments are satisfactory for conditions where only one or a few applications of the medicinal agents are necessary, certain conditions require more frequent doses and such treatments are inconvenient to patients. In contrast, ophthalmic medicinal agents in solid forms allow a high weight of drug per administered volume. This is particularly advantageous when a large amount of drug must be administered per dose or when the volume is constrained, as in intraocular injections. Additionally, the solid state also renders the compound less sensitive to solution-mediated chemical degradation.

Direct injection into a sensitive and delicate structure like the eye has certain challenges and attendant difficulties. There are a number of procedures and devices that have been developed for the controlled injection of an implant into a tissue, such as an eye. However, improved procedures and devices would be beneficial.

SUMMARY OF THE INVENTION

This invention discloses an injector device that delivers an implant into a tissue. In certain embodiments, the injector device is fitted with detachable protectors to secure the device during events such as handling and shipping.

In the present invention, the term "proximal" is used to refer to that portion of an element closest to the physician's hand depressing the plunger when being utilized to inject an implant. The term "distal" is used herein to refer to that portion of an element farthest from the physician's hand. The term "transverse" is used herein to refer to a plane orthogonal to a longitudinal axis of the injector device. The term "injector" is broadly intended to comprise all types of dispensing apparatus that include a hollow shaft and a plunger. The injector of the current invention is not restricted to medical use, and may be utilized for suitable non-medical applications such as industrial or home usages.

In a first aspect of this invention, the invention relates to an injector device comprising a syringe barrel that defines a central axial cavity coaxially coupled to a cannula needle that also defines a central axial cavity, such that the central axial cavities of the cannula needle and the syringe barrel are in communication with each other. An implant may be disposed in the central axial cavity of the cannula needle from a distal end of the needle. Furthermore, a plunger coupled to a pusher rod may be disposed in the central axial cavity of the syringe barrel extending beyond a proximal end of the syringe barrel. The pusher rod is adapted to enter the central axial cavity of the cannula needle such that the implant can be ejected from the distal end of the needle when the plunger is depressed into the syringe barrel. Furthermore, to control the needle's penetration depth, a stop is disposed between the syringe barrel and the cannula needle. A positive cross-sectional area difference between the stop and the needle prevents the needle from penetrating into a tissue beyond the distance defined by the distal end of the needle and a distal end of the stop.

In another aspect of the invention, an injector device as described above further comprises a removable catch coupled to the device to releasably restrict the movement of the plunger into the syringe barrel. In turn, this prevents the pusher rod from being prematurely depressed and ejecting the implant from the cannula needle via its distal end. In one such embodiment, a catch may be disposed around a portion of the plunger between the proximal end of the syringe barrel and an end-piece at a proximal end of the plunger. Physical interaction among the catch, the plunger's end-piece and the proximal end of the syringe barrel blocks the plunger from further entering the syringe barrel when the proximal end of the syringe barrel and the plunger's end-piece contact the catch. Accordingly, an effective catch distance is defined as a difference between a length of the plunger that extends beyond the proximal end of the syringe barrel after further plunger-depression movement is curtailed by the catch and a length of the plunger that extends beyond the proximal end of the syringe barrel in a fully depressed position in the absence of the catch. The catch should restrain the plunger at a position such that, at minimum, the effective catch distance is at least as long as the longitudinal length of the implant. Thus, the effective catch distance is such that, for an implant having a predetermined longitudinal length, the implant cannot be ejected from the cannula needle when the catch is engaged.

This invention also relates to a disengageable block that reversibly obstructs the implant from exiting the cannula needle of the injector device from the needle's distal end. The block may be a hook-shaped block wire with one end that penetrates the distal end of the cannula needle. In such embodiments, a second end of the wire may be secured to a portion of the injector device, such as by means of a tubular ring disposed around a periphery of a portion of the injector device.

In yet another aspect of the invention, a method is disclosed for the assembly of the injector device comprising disposing the plunger and pusher rod unit in the central axial cavity of the syringe barrel, optionally coupling the releasable catch to the injector device, fitting the pusher rod into a proximal end of the cannula needle, and operatively coupling the needle to the syringe barrel, followed by disposing the implant in the cannula needle. Optionally, the method may include coupling a removable block to the injector device to obstruct the implant from exiting the needle, and/or fitting a cap around the needle.

Furthermore, a method is disclosed for employing the injector device by first removing the cap, the block, and the catch if they are present, inserting the cannula needle into a tissue to a depth where the stop contacts the tissue's surface, then depressing the plunger into the syringe barrel to expel the implant from the cannula needle into the tissue.

In one embodiment, the injector device of the present invention is utilized for injecting an implant into an eye. Such a method specifically may comprise the use of a cannula needle adapted to make incisions into the tissue of an eye. The needle and stop are also adapted to penetrate only a predetermined depth into the eye. If a catch is coupled to the intraocular injector device, the effective distance is such that, for an implant having a predetermined longitudinal length, the implant cannot be ejected from the cannula needle of the intraocular injector device when the catch is engaged.

BRIEF DESCRIPTION OF THE DRAWINGS

FIG. 3 depicts a transverse cross-sectional view of an array of finger-grip configurations for an injector device.

FIG. 4 illustrates an exploded perspective view of an injector device's head element, whose alternative embodiments are shown in FIG. 4A and FIG. 4B.

FIG. 5 depicts a variety of stop configurations including FIG. 5A, a stub, FIG. 5B, an integrally formed tubing from a housing element, and FIG. 5C, a short tubular ring.

FIG. 7 illustrates a transverse cross-sectional view of an array of stopper configurations for an injector device.

FIG. 8 depicts a series of injector device configurations, wherein

FIG. 9 depicts a series of removable catch configurations including FIG. 9A, a protruding stub, FIG. 9B, a tubular ring, FIG. 9C, a clip, and FIG. 9D, a lodging pin.

FIG. 10 illustrates a variety of disengageable block configurations.

DETAILED DESCRIPTION

The device and method described herein provide an injector device capable of delivering an implant into a tissue. In certain embodiments, the injector device is fitted with detachable guards to secure the device during events such as handling and shipping. It will be understood by one of ordinary skill in the art that the device and method described herein can be adapted and modified for other suitable applications and that such other additions and modifications will not depart from the scope hereof.

Figure 1:
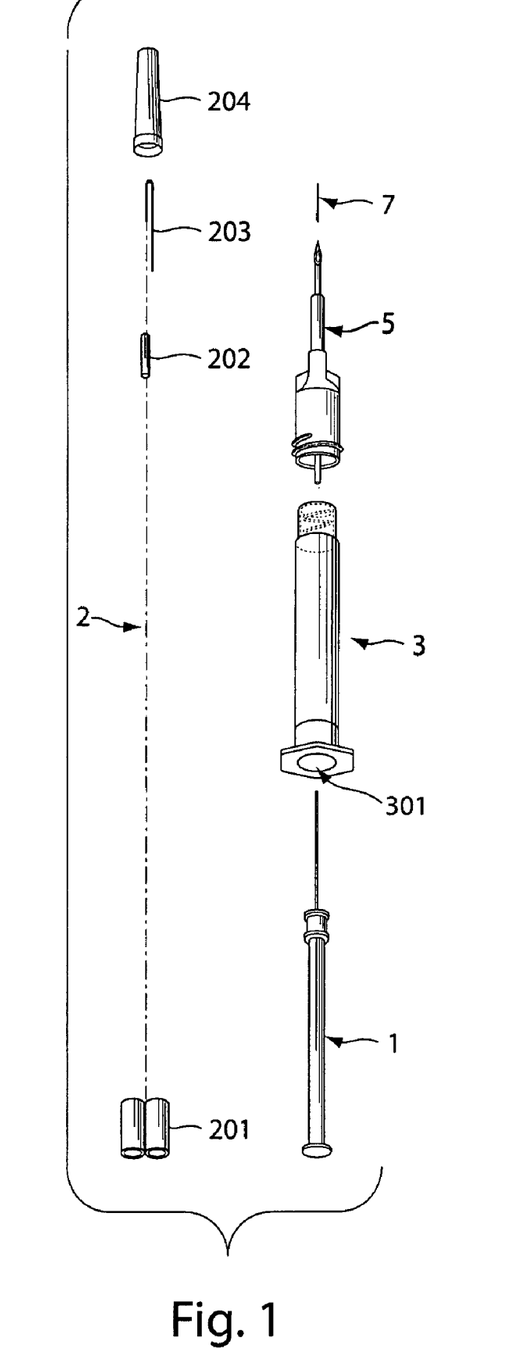
FIG. 1 is an exploded perspective view of an injector device of the present invention including a set of optional, disengageable elements.

FIG. 1 is an exploded perspective view of an injector device of the present invention. The injector comprises a syringe barrel 3, an inserter element 1 disposed in a central axial cavity 301 defined by the syringe barrel 3, a head element 5 coaxially coupled to the syringe barrel 3, and an implant 7 disposed in the injector device thereof. An array of disengageable elements 2 may be optionally coupled to the injector device to secure the device during handling.

Figure 2:
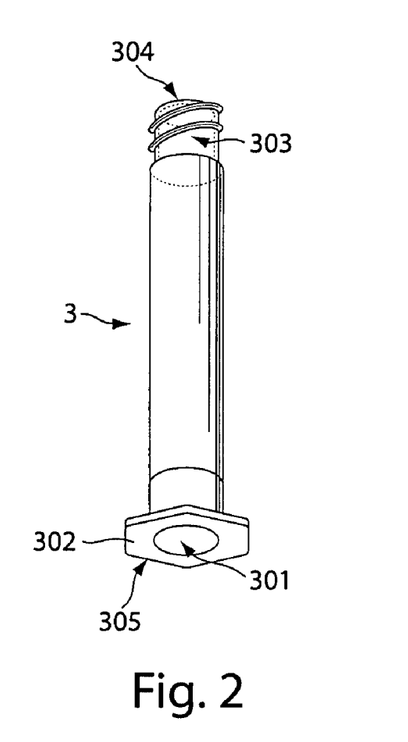
FIG. 2 illustrates an exploded perspective view of an injector device's syringe barrel.
Figure 3A:
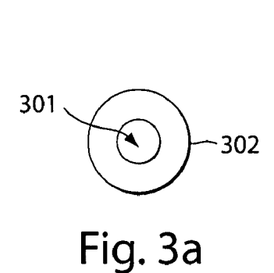
FIG. 3A-3C respectively show a circular cross-sectioned, triangular cross-sectioned, and rectangular cross-sectioned finger-grip configuration pertaining to a circular cross-sectioned syringe barrel.
Figure 3B:
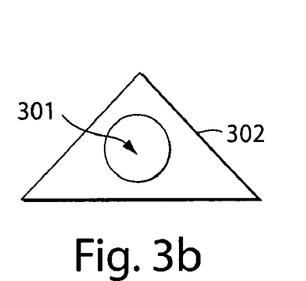
Figure 3C:
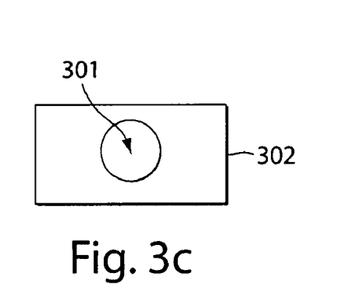
Figure 3D:
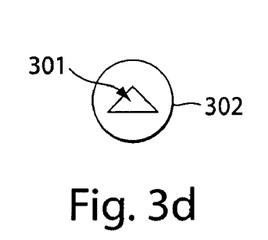
FIG. 3D-3F show a circular cross-sectioned, triangular cross-sectioned, and rectangular cross-sectioned finger-grip configuration respectively pertaining to a triangular cross-sectioned, rectangular cross-sectioned and triangular cross-sectioned syringe barrel.
Figure 3E:
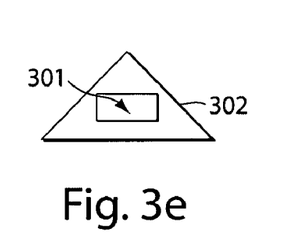
Figure 3F:
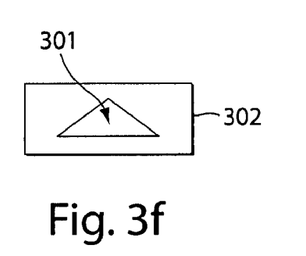

FIG. 2 depicts an exploded view of the syringe barrel 3 that defines a central axial cavity 301, a distal end 304 and a proximal end 305. The central axial cavity 301 may have a circular transverse cross-sectional shape, as shown in the current embodiment, although the cross-sectional shape may be square, triangular, polygonal, or any other suitable shape. Calibration lines may be optionally provided on the syringe barrel 3 to mark the progress of the inserter element 1 as it is depressed into the syringe barrel 3. A finger-gripping portion 302 may be integrally formed from the syringe barrel 3, as shown, or may be mechanically, chemically or otherwise coupled to the syringe barrel 3. The finger-gripping portion 302 is adapted to allow the syringe barrel 3 to be held and to provide a resist when the inserter element 1 is being depressed into the syringe barrel 3. Hence, any of a variety of shapes may be selected for the finger-gripping portion 302 to provide suitable finger placement during syringe handling.

FIG. 3 shows an array of exemplary shapes of the finger-gripping portion 302 depicted from a transverse viewing perspective. These shapes may be circular, triangular, rectangular, or any other suitable shape. The distal end of the syringe barrel 3 may include threads 303 adapted to engage the head element 5.

FIG. 4 shows an exploded view of the head element 5 which includes a housing 501 that defines a central axial cavity 502, a distal end 509 and a proximal end 512. An outwardly extending flange 503 projects from the housing's external peripheral surface and is adapted to engage the threads 303 on the distal end 304 of the syringe barrel 3 to coaxially couple the head element 5 to the syringe barrel 3. Those of ordinary skill in the art will recognize that a variety of other coupling mechanisms may be used to securely engage the head element 5 to the syringe barrel 3 during injection. In alternative embodiments, the head element 5, excluding the housing 501, may be coupled directly to the distal end 304 of the syringe barrel 3 without the aid of the housing 501, or may be integrally formed with the syringe barrel 3.

The head element 5 includes a cannula needle 505 that defines a central axial cavity 506, a distal end 508 and a proximal end 511. The cannula needle 505 may be formed from, for example, between about 18- and 30-gauge tubing. The cannula needle 505 may have a beveled tip at its distal end 508 disposed at a pre-determined angular relation to the longitudinal axis of the needle's central axial cavity 506. Although the cannula needle 505 preferably has a straight longitudinal profile, other suitable longitudinal needle shapes may be used. The needle 505 may be made of any suitably rigid material such as metal or metal alloys, for example stainless steel or the like. An implant 7 is adapted to fit in the central axial cavity 506 of the cannula needle 505 from its distal end 508 as depicted in FIG. 5A. The implant 7 may be of any solid composition, e.g., for releasing drug or other agents.

The head element 5 also includes a stop 504, having a distal end 510, and disposed between the distal end 509 of the housing 501 and the distal end 508 of the cannula needle 505. A positive transverse cross-sectional area difference between the stop 504 and the needle 505 prevents the needle 505 from penetrating a tissue beyond its longitudinal length that extends from the distal end 510 of the stop 504. This longitudinal length is defined as a penetration depth 507 of the needle 505. The stop 504 may be integrally formed from the housing 501 or, in another embodiment, securely coupled to the housing 501. In the present embodiment as depicted in FIG. 4, the stop comprises a tubular collar 504 coaxially situated between the distal end 509 of the housing 501 and the distal end 508 of the cannula needle 505. Those of ordinary skill in the art will recognize that there are a variety of stop configurations suitable for controlling the penetration depth of the needle 505.

Figure 5A:
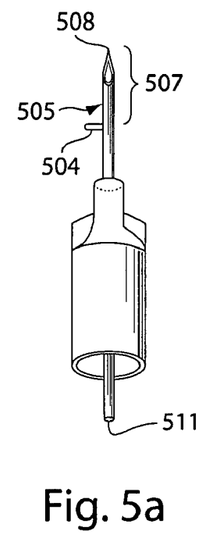
Figure 5B:
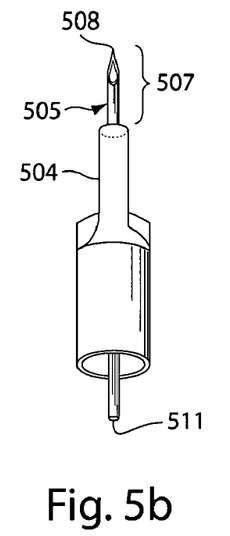
Figure 5C:
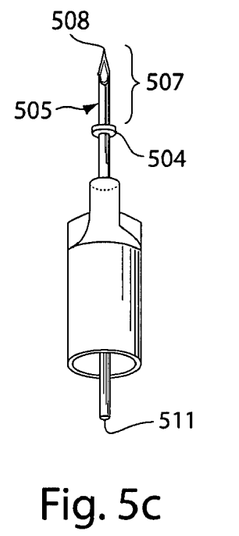

Exemplary configurations of the stop 504 are presented in FIG. 5 from a viewing perspective longitudinal to the injector device. As shown in FIG. 5A, one exemplary configuration comprises a projection from a surface of the cannula needle 505. The penetration depth 507 of the needle 505, in this case, is the longitudinal distance from that projection to the distal end 508 of the needle 505. Yet another configuration as shown in FIG. 5C depicts a short tubular ring 524 that is disposed around a periphery of a portion of the needle 505 and situated at a position where the needle's penetration depth 507 is defined by a longitudinal distance from the tubular ring 524 to the distal end 508 of the needle 505.

Figure 4A:
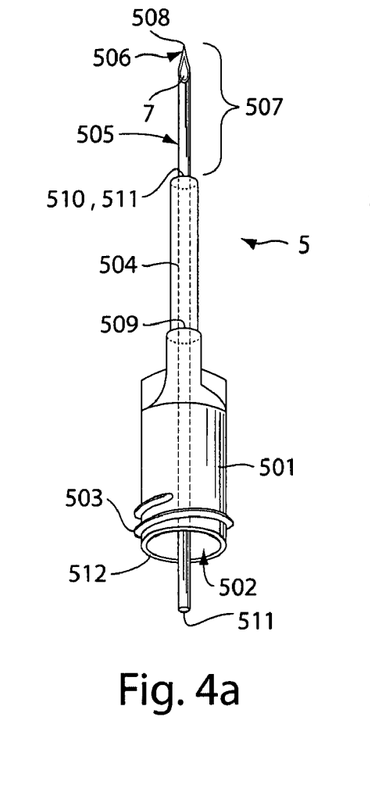
Figure 4B:
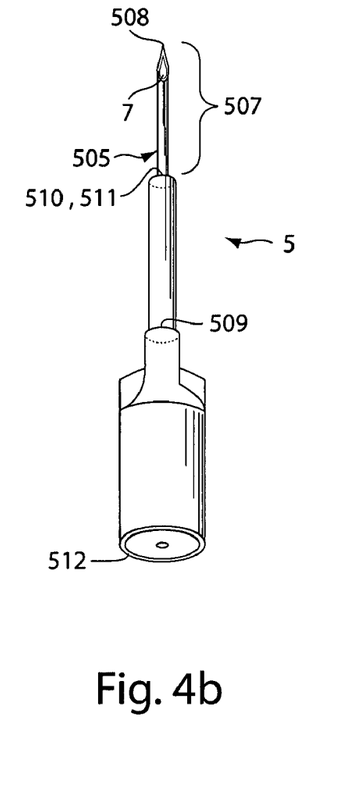

In the embodiment depicted in FIG. 4A, a connected passageway is formed by the tubular collar 504 in communication with the central axial cavity 502 of the housing 501. In one configuration as illustrated in FIG. 4A, a cannula needle 505 may be disposed in the passageway and situated in such a manner that its proximal end 511 extends beyond the proximal end 512 of the housing 501 and its distal end 508 extends beyond the distal end of the tubular collar 504. Alternatively, a cannula needle 505 may be coaxially coupled to the distal end 510 of the tubular collar 504 such that the needle's central axial cavity 507 is in communication with the connected passageway. This configuration is depicted in FIG. 4B. In either configuration, the cannula needle 505 is coaxially positioned with respect to both the tubular collar 504 and the housing 501. In both configurations, the penetration depths 507 of the needles can be made to be about equal.

Figure 6:
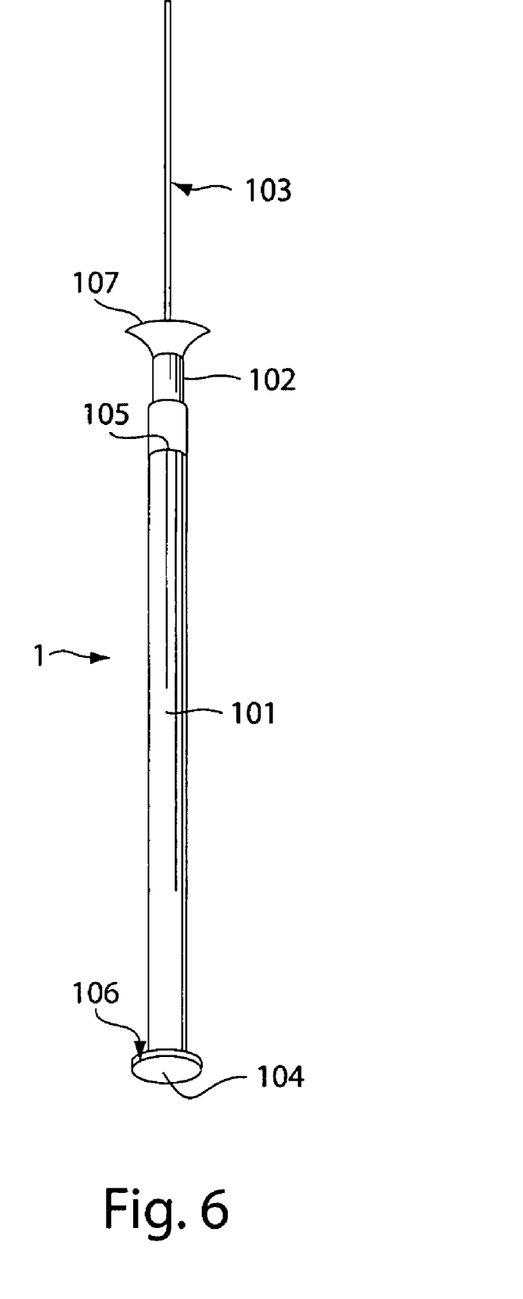
FIG. 6 shows an exploded perspective view of an injector device's inserter element.

As shown in an exploded view in FIG. 6, the inserter element 1 includes a plunger 101, having a distal end 105 and a proximal end 106. The plunger's transverse cross-sectional shape may vary as long as it fits into the central axial cavity 301 of the syringe barrel 3. An end-piece 104 may be integrally formed or securely coupled to the plunger 101. The end-piece 104 facilitates the depression of the plunger 101 into the syringe barrel 3. Hence the shape of the end-piece 104 may vary as long as it permits plunger-depressing movement. The plunger 101 is preferably adapted to extend beyond the syringe barrel's proximal end 305 when fully depressed.

In addition, the inserter element 1 includes a stopper 102, having a distal end 107, and may be coupled to the distal end 105 of the plunger 101. To guide the plunger 101 during depression, the stopper 102 assumes a shape that allows it to fit securely within the central axial cavity 301 of the syringe barrel 3. In contrast to stoppers utilized in syringes for the injection of liquid, the stopper 102 of the present invention does not need to form an air-tight seal with the inner peripheral surface of the syringe barrel 3, and in fact, may define passages that permit the free movement of air during the depression of the plunger 101. In the embodiment as depicted in FIG. 6, the stopper 102 is a single ring-shaped cylindrical disc whose shape allows it to fit securely within a cylindrical cavity 301 of a syringe barrel 3.

Figure 7A:
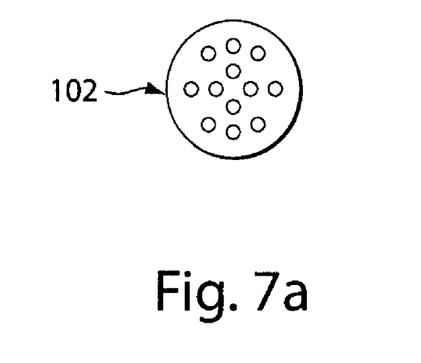
FIG. 7A illustrates a circular cross-sectioned stopper with apertures.
Figure 7B:
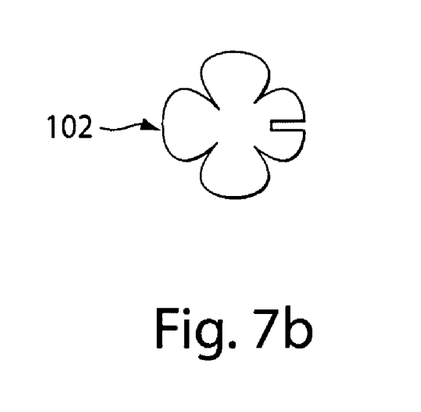
FIG. 7B, a stopper with a petal-like cross-sectional configuration.
Figure 7C:
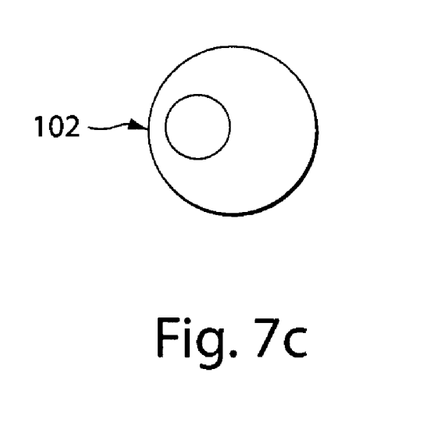
FIG. 7C, a circular cross-sectioned stopper with an off-center circular opening.

Other stopper arrangements are suitable for the purpose of the current invention, and certain examples of such stopper arrangements are as depicted in FIG. 7 from a distal-end, transverse cross-sectional viewing perspective. One exemplary configuration in FIG. 7A comprises a cylindrical-bodied stopper 102 having apertures on the cross section of its distal end 107 to facilitate air passage. In another configuration in FIG. 7B, a cylindrical-bodied stopper 102 has a petal-shaped cross section at its distal end 107, whose petals fit securely within a syringe barrel's central axial cavity 301. These stopper configurations may be suitably modified to accommodate syringe barrels whose transverse cross-sectional shapes are other than circular.

Referring once again to FIG. 6, the inserter element 1 also includes a pusher rod 103, having a distal end 109, and is coupled to the distal end 107 of the stopper 102. The pusher rod 103 is adapted to enter the proximal end 511 of the cannula needle 505 and to eject the embedded implant when the plunger 101 is depressed into the syringe barrel 3. Alternative means of expelling the implant 405 are possible. For example, in place of a pusher rod 103, a second plunger may be coaxially enclosed in the syringe barrel whose distal end is adapted to enter the proximal end of the cannula needle. The proximal end of the second plunger is coupled to a second stopper similar to the first stopper coupled to the distal end of the first plunger, where said first and second stoppers form air-tight seals with the interior peripheral surface of the syringe barrel. A volume of air separates the first and second stoppers in the syringe barrel. In operation, when the first plunger is drawn back on the syringe barrel, the volume of air between the stoppers increases. Depressing the first plunger into the syringe barrel decreases that volume of air, thus generating a pressure that propels the second plunger to advance into the cannula needle and dispense the implant therein.

In a preferred embodiment as depicted in FIG. 6, the inserter element 1 has a longitudinal length approximately equal to or greater than the distance between the proximal end 305 of the syringe barrel 3 and the distal end 508 of the needle 505. More particularly, the inserter element 1 is configured such that the distal end 109 of the pusher rod 103 is at or near the distal end 508 of the needle 505 when the inserter element 1 is fully depressed into the syringe barrel 3.

The syringe barrel 3, the finger-gripping portion 302, the plunger 101, the end-piece 104, the housing 501 and the stop 504 can be prepared from hard plastic, glass, stainless steel or other suitably durable materials that may be transparent, translucent, opaque, or non-opaque. All the aforementioned pieces may have the same or different material compositions. For example, the finger-gripping portion 302 may or may not be made of the same material as the syringe barrel 3, the end-piece 104 may or may not have the same material composition as the plunger 101, and the housing 501 may or may not be made of the same material as the stop 502. The pusher rod 103 is made of a suitably rigid material, such as stainless steel or hard plastic, so that it can eject an implant 7 from the cannula needle 505 via its distal end 508 when the plunger 101 is depressed. The stopper 504 may be made of an elastic material such as rubbers or synthetic rubbers, or, in some embodiments, a hard, non-elastic material. All the above pieces can be prepared from heat- or irradiation-stable materials for reuse or prepared as disposables for single-use applications.

In certain embodiments, to prevent the pusher rod 103 from being depressed and ejecting the implant 7 from the cannula needle 505, a removable catch 201 can be coupled to the injector device to restrict plunger movement. For example, in the embodiment depicted in FIG. 8B, a catch 201 can be disposed around a portion of the plunger 101 between the proximal end 305 of the syringe barrel 3 and the end-piece 104 at the proximal end 106 of the plunger 101. Physical interaction among the catch 201, the plunger's end-piece 104 and the proximal end 305 of the syringe barrel 3 blocks the plunger 101 from further entering the syringe barrel 3 when the proximal end 305 of the syringe barrel 3 and the plunger's end-piece 104 contact the catch 201.

Figure 8A:
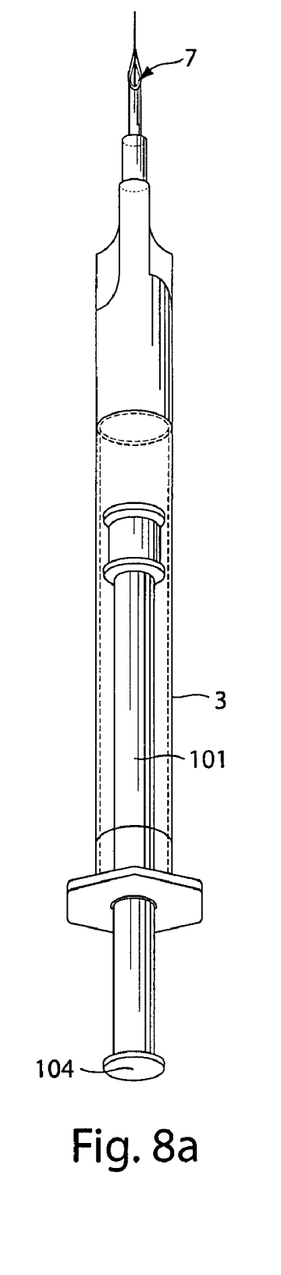
FIG. 8A depicts an injector device configured with an implant disposed therein.
Figure 8B:
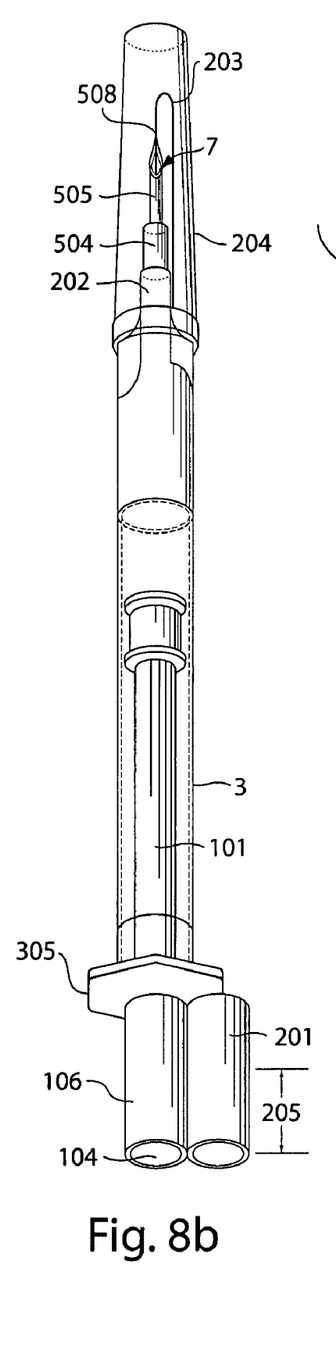
FIG. 8B depicts an injector device configured with its set of disengageable elements coupled thereto.
Figure 8C:
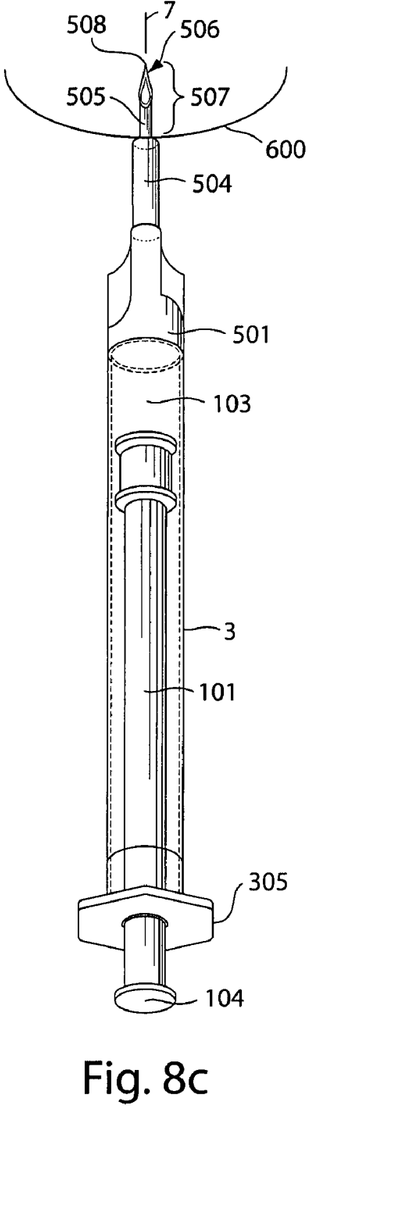
FIG. 8C depicts an injector device configured for injection.
Figure 9A:
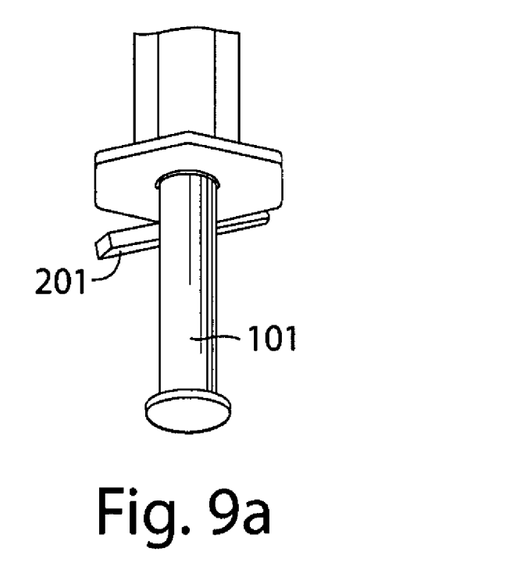
Figure 9B:
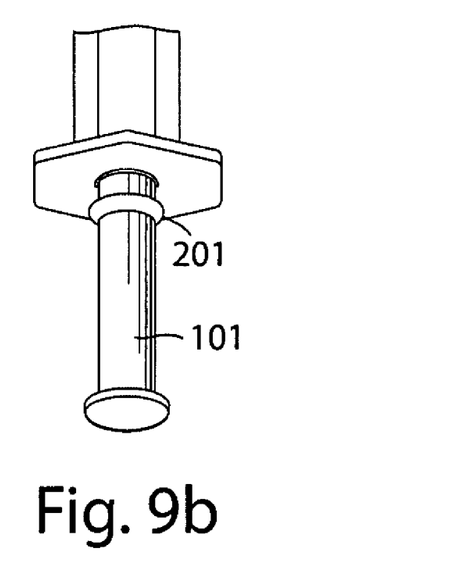
Figure 9C:
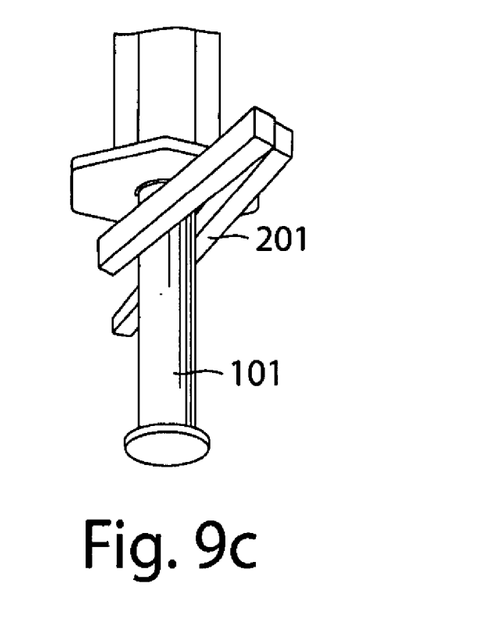
Figure 9D:
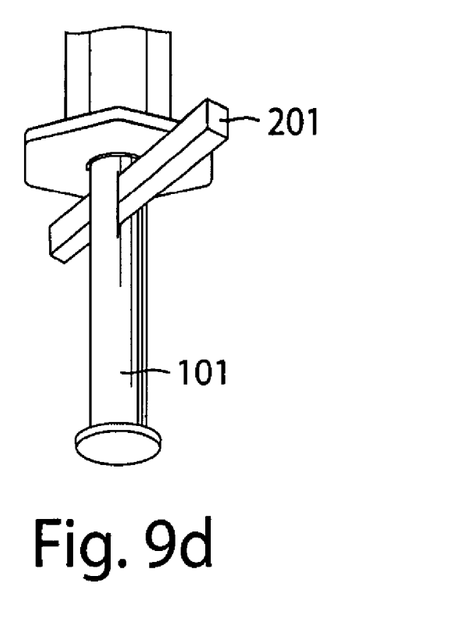

Catches of various shapes and configurations can be used to releasably restrict the plunger's 101 entry into the syringe barrel 3 as depicted in FIG. 9. Another catch arrangement as shown in FIG. 9A consists of a stub that can be securely locked into place on a portion of the plunger's peripheral surface by means such as magnets or threads. Yet in another arrangement as shown in FIG. 9D, a pin may be used that pierces a cross section of the plunger 101. A longitudinal length of the pin is larger than a maximum cross-sectional extend of the syringe barrel's central axial cavity 301, hence barring the plunger 101 from further advancement when the pin contacts the distal end 304 of the syringe barrel 3. Accordingly, an effective catch distance 205, as illustrated in FIGS. 8B and 8C, may be defined as a difference between a length of the plunger 101 that extends beyond the proximal end 305 of the syringe barrel 3 after further plunger-depression movement is curtailed by the catch 201 and a length of the plunger 101 that extends beyond the proximal end 305 of the syringe barrel 3 in a fully depressed position in the absence of the catch 201. The catch 201 should restrain the plunger 101 at a position such that, at minimum, the effective catch distance 205 is at least as long as the longitudinal length of the implant 7. Hence, the effective catch distance is such that the distal end 109 of the injector device's push rod 103 is at or near the distal end 508 of the needle 505 when the insert element 1 is fully depressed into the syringe barrel 3.

In certain embodiments, a disengageable block 203, which may be made of a suitably rigid material such as stainless steel, hard plastic, or the like, may be utilized to reversibly obstruct the implant 7 from exiting the cannula needle 505 from its distal end 508 as shown in FIG. 8B. The block may be, for example, a hook-shaped wire 203 with one end penetrating the distal end 508 of the cannula needle 505. A second end of the wire 203 is secured to a portion of the injector device, e.g., by means of a securing member 202, such as a tubular ring, disposed around a periphery of a portion of the injector, such as around the tubular collar 504. The securing member may be made of any malleable material such as rubber, synthetic rubber, soft plastic, metal, or the like. In the present embodiment, the hook-shaped block wire 203, which is anchored to the injector device using the tubular ring 202, protects the needle 505 from being deflected during handling.

Figure 10A:
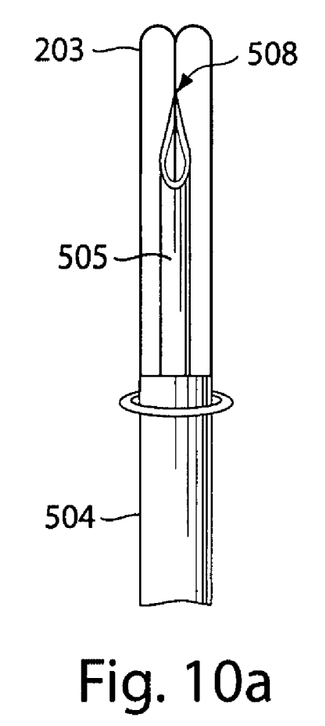
FIG. 10A illustrates a three-prong block wire.
Figure 10B:
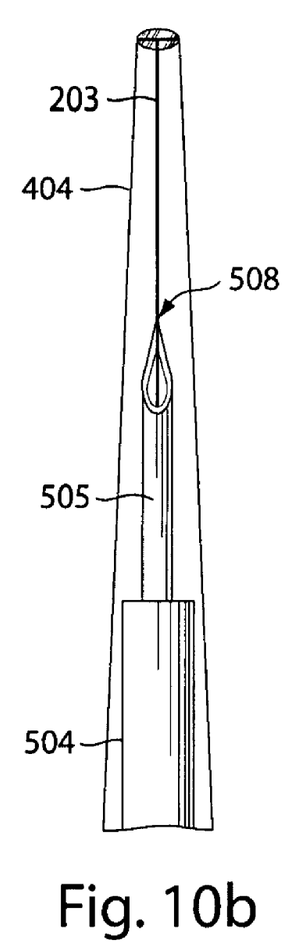
FIG. 10B, a straight block wire coupled to a cap.
Figure 10C:
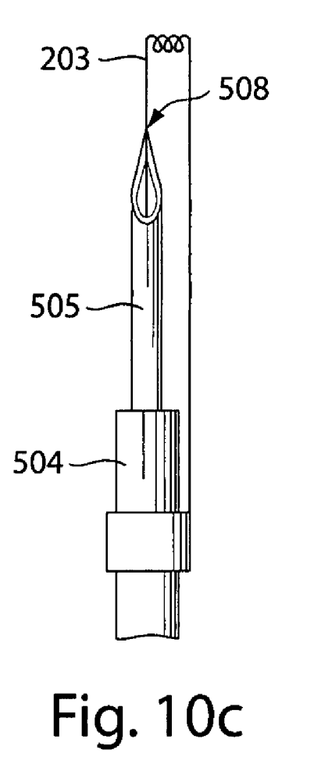
FIG. 10C, a bent, partially-spiraling block wire.

A variety of modifications, as shown in FIG. 10, can be made to the block wire 203 and tubular ring 202 configuration that obstruct the implant 7 from exiting the needle 505 and/or protect the integrity of the needle 505. One embodiment of the block, as shown in FIG. 10A, depicts a three-prong block wire. The center prong penetrates the distal end 508 of the cannula needle 505 and the block wire is anchored to the injector device by inserting the side prongs through two oppositely situated loops on the periphery of the stop. In an alternative embodiment, a straight block wire is coupled to the internal peripheral surface of a distal end of a cap. Thus, when the cap is fitted onto the head element, the block wire penetrates the distal end 508 of the cannula needle 505 to prevent the implant 7 from exiting.

The injector device as described above can be prepared by any suitable method, and the various parts assembled in any suitable order. A preferred assembly method comprises disposing the inserter element 1 into the central axial cavity 301 of the syringe barrel 3 from its proximal end 305, optionally coupling the releasable catch 201 to the injector device, then fitting the distal end 109 of the pusher rod 103 into the proximal end 511 of the cannula needle 505 and operatively coupling the head element 5 to the syringe barrel 3, followed by disposing the implant 7 in the cannula needle 505. Optionally, the above method may include fitting the securing elements such as the tubular ring 202 around the circumference of the tubular collar 504, optionally penetrating one end of the hook-shaped block wire 203 into the distal end 508 of the cannula needle 505 and securing a second end of the block wire 203 to the tubular ring 202, and, optionally, fitting the cap 204 onto the head element 5 thereof. The assembled injector device, including all optional elements, is depicted in FIG. 8B.

The injector device may be employed by first removing the cap 204, the block 203 and the catch 201 if they are present, inserting the cannula needle 505 into a tissue to a depth where the stop 504 contacts the surface of the tissue, then depressing the plunger 101 into the syringe barrel 3 to expel the implant 7 from the distal end 508 of the cannula needle 505 into the tissue.

In one embodiment of the injector device, depicted in FIG. 8C, the device is designed to deliver a drug to an eye 600. In particular, the needle 505 of the intraocular injector device is adapted to penetrate a sclera of the eye 600. The needle 505 may be a straight 25-gauge cannula needle and have, for example, a beveled tip at its distal end 508, e.g., disposed at an angle of about between 10 and 13 degrees, preferably about 11.5 degrees, in relation to the longitudinal axis of the needle's central axial cavity 506. The stop of the depicted device comprises a tubular collar 504 that is coaxially coupled to the housing 501 of the device and forms a common passageway with the housing's central axial cavity 502, wherein the needle 505 is disposed and situated in such a manner that its penetration depth 507 is about 0.25 to 0.35 cm. The inserter element 1 of the intraocular injector device preferably has a longitudinal length approximately equal to or greater than the distance between the proximal end 305 of the device's syringe barrel 3 and the distal end 508 of its needle 505, and is preferably configured such that the distal end 109 of the device's pusher rod 103 is at or near the distal end 508 of the needle 505 when the inserter element 1 is fully depressed into the syringe barrel 3.

In addition, as depicted in FIGS. 8B and 8C, the optional removable catch 201 of the intraocular injector device produces an effective catch length 205 between about 0.3 and 0.9 cm as the proximal end 305 of the device's syringe barrel 3 and the end-piece 104 of the device's plunger 101 both contact the catch 201. Hence the device's implant 7 may have a longitudinal length of about 0.1 to 0.9 cm.

The optional disengageable block of the device may comprise a hook-shaped block wire 203 as depicted in FIG. 8B. When coupled to the injector device, one end of the block wire 203 penetrates the distal end 508 of the needle 505 and a second end is secured to a portion of the tubular collar 504 by means of a tubular ring 202, though any other configuration that effectively blocks exit of the implant 7 from the distal end 508 of the cannula needle 505 may alternatively be employed. The cap 204 of the device may optionally be fitted onto the device's head element 5 to enhance needle protection during handling.

Thus, the invention generally provides an injector device possessing optional protector elements designed for the device's secured handling. The purpose of the above description and examples is to illustrate some non-limiting embodiments of the present invention. It will be apparent to those skilled in the art that various modifications and variations may be made to the device and method of the present invention without departing from the spirit or scope of the invention.

All publications and patents cited herein are hereby incorporated by reference in their entirety.

What is claimed is:

1. An injector device comprising:
   a syringe barrel defining a central axial cavity, and having a distal end and a proximal end;
   a cannula needle having a distal end and a proximal end coaxially coupled to the distal end of the syringe barrel, and defining a central axial cavity in communication with the central axial cavity of the syringe barrel;
   a plunger having a distal end and a proximal end, disposed in the central axial cavity of the syringe barrel, and extending beyond the proximal end of the syringe barrel when fully depressed;
   a pusher rod coupled to the distal end of the plunger and adapted to enter the central axial cavity of the cannula needle when the plunger is depressed into the syringe barrel;
   a stop disposed at the proximal end of the cannula needle, coupled to the distal end of the syringe barrel, and having a portion that extends beyond a cross section of the needle;
   a disengageable catch coupled to a portion of the plunger and that blocks the plunger from entering the syringe barrel beyond a pre-determined point;
   an implant disposed in the central axial cavity of the cannula needle between the pusher rod and the distal end of the needle; and
   a disengageable block that obstructs the implant from exiting the distal end of the cannula needle the block having a first end that penetrates the distal end of the cannula needle and a second end secured to an outside portion of the injector device.

2. The injector according to claim 1, wherein the stop includes a tubular collar and the tubular collar and the cannula needle are coaxially positioned, and a positive cross-sectional area difference between the tubular collar and the needle prevents penetration of the needle into a tissue beyond a pre-determined depth.

3. The injector according to claim 1, wherein the catch is disposed around a portion of the plunger between the proximal end of the syringe barrel and an end-piece at the proximal end of the plunger and interaction among the catch, the proximal end of the syringe barrel, and the plunger's end-piece blocks the plunger from further entering the syringe barrel when the proximal end of the syringe barrel and the plunger's end-piece contact the catch.

4. The injector according to claim 3, wherein an effective catch distance is defined as a difference between a length of the plunger that extends beyond the proximal end of the syringe barrel after further plunger-depression movement is restrained by the catch and a length of the plunger that extends beyond the proximal end of the syringe barrel in a fully depressed position in the absence of the catch.

5. The injector according to claim 4, wherein the catch retrains the plunger at a position such that, at minimum, the effective catch distance is at least as long as a longitudinal length of the implant.

6. The injector according to claim 1, wherein the block is a wire having a hook shape, and a first end of the wire penetrates the distal end of the cannula needle and a second end of the wire is secured to a portion of the injector device.

7. The injector according to claim 1, wherein the block is a wire having a hook shape, and a first end of the wire penetrates the distal end of the cannula needle and a second end of the wire is secured by means of a tubular ring disposed around a periphery of a portion of the injector device.

8. A method of assembling an injector device comprising:
   providing a syringe barrel defining a central axial cavity, and having a distal end and a proximal end;
   providing a plunger having a distal end and a proximal end, and adapted to enter the central axial cavity of the syringe barrel;
   providing a cannula needle defining a central axial cavity, and having a distal end and a proximal end;
   disposing a pusher rod coupled to the plunger in the central axial cavity of the syringe barrel, having a portion of the pusher rod extends beyond the distal end of the syringe barrel, and having a portion of the plunger extends beyond the proximal end of the syringe barrel;
   coupling a removable catch to the injector device;
   fitting the pusher rod into the central axial cavity of the cannula needle and operatively coupling the cannula needle to the distal end of the syringe barrel;
   placing an implant within the central axial cavity of the cannula needle between the pusher rod and the distal end of the needle; and
   coupling a disengageable block to the injector device.

9. The method according to claim 8, wherein coupling the removable catch comprises disposing the catch to a portion of the plunger between the proximal end of the syringe barrel and an end-piece at the proximal end of the plunger and the removable catch is adapted to interact with the proximal end of the syringe barrel and the plunger's end-piece to block the plunger from further entering the syringe barrel when the proximal end of the syringe barrel and the plunger's end-piece contact the catch.

10. The method according to claim 9, wherein coupling the removable catch creates a catch distance defined as a difference between a length of the plunger that extends beyond the proximal end of the syringe barrel after further plunger-depression movement is restrained by the catch and a length of the plunger that extends beyond the proximal end of the syringe barrel in a fully depressed position in the absence of the catch.

11. The method according to claim 10, wherein the removable catch is adapted to retrain the plunger at a position such that, at minimum, the effective catch distance is at least as long as a longitudinal length of the implant.

12. The method according to claim 8, wherein the disengageable block is a hook-shaped block wire with a first end disposed in the distal end of the cannula needle and a second end of the block wire is coupled to a portion of the injector device.

13. The method according to claim 8, wherein the disengageable block is a hook-shaped block wire with a first end disposed in the distal end of the cannula needle and a second end of the block wire is secured by means of a tubular ring around a periphery of a portion of the device.

14. A method of injecting an implant using an injector device, comprising:
   providing an injector device of claim 1;
   removing the block if it is present;
   removing the catch if it is present;
   inserting the cannula needle into a tissue to a depth where surface of the tissue contacts the stop; and
   depressing the plunger into the syringe barrel to eject the implant via the distal end of the cannula needle into the tissue.

15. The method according to claim 14, wherein the tissue is an eye.

16. The method according to claim 15, wherein the cannula needle is a 25-gauge needle and the cannula needle has a beveled tip adapted to penetrate a sclera of an eye.

17. The method according to claim 16, wherein the stop of the injector device is a tubular collar.

18. The method according to claim 17, wherein the tubular collar and the cannula needle are coaxially positioned, and a positive cross-sectional area difference between the tubular collar and the needle prevents penetration of the needle into the eye beyond a pre-determined depth of about 0.25 to 0.45 centimeters.

19. The method according to 18, wherein the catch is disposed around a portion of the plunger between the proximal end of the syringe barrel and an end-piece at the proximal end of the plunger.

20. The method according to 19, wherein the interaction among the catch, the proximal end of the syringe barrel, and the plunger's end-piece blocks the plunger from further entering the syringe barrel when the proximal end of the syringe barrel and the plunger's end-piece contact the catch.

21. The method according to claim 20, wherein an effective catch distance, defined as a difference between a length of the plunger that extends beyond the proximal end of the syringe barrel after further plunger-depression movement is restrained by the catch and a length of the plunger that extends beyond the proximal end of the syringe barrel in a fully depressed position in the absence of the catch, is about 0.6 centimeters.

22. The method according to claim 21, wherein a longitudinal length of the implant is between 0.1 to 0.6 centimeters.

23. The method according to claim 22, wherein the disengageable block is a hook-shaped wire and a first end of the wire penetrates the distal end of the cannula needle and a second end of the wire is secured to a portion of the intraocular injector device.

24. The method according to claim 22, wherein the disengageable block is a hook-shaped wire and a first end of the wire penetrates the distal end of the cannula needle and a second end of the wire is secured by means of a tubular ring disposed around a periphery of a portion of the intraocular injector device.

\* \* \* \* \*